United States Patent
Labidalle et al.

(10) Patent No.: US 6,686,360 B2
(45) Date of Patent: Feb. 3, 2004

(54) N-BENZYLPIPERAZINE COMPOUNDS

(75) Inventors: Serge Labidalle, Pinsaguel (FR); Jean-Paul Tillement, Bois le Roi (FR); Bernard Testa, Lausanne (CH); Roméo Cecchelli, Villeneuve d'Ascq (FR); Alain Le Ridant, Neuilly sur Seine (FR); Catherine Harpey, Paris (FR); Michael Spedding, Le Vesinet (FR); Esther Schenker, Paris (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 10/195,948

(22) Filed: Jul. 16, 2002

(65) Prior Publication Data

US 2003/0158207 A1 Aug. 21, 2003

(30) Foreign Application Priority Data

Jul. 16, 2001 (FR) .............................. 01 09454

(51) Int. Cl.⁷ .................... A61K 31/495; A61K 31/506; C07D 295/155; C07D 403/04
(52) U.S. Cl. ............................ 514/252.12; 514/252.14; 514/252.19; 514/255.03; 544/295; 544/393; 544/394; 544/399; 544/400
(58) Field of Search ................................ 544/295, 394, 544/393, 399, 400; 514/252.12, 252.14, 252.19, 255.03

(56) References Cited

U.S. PATENT DOCUMENTS 6,479,495 B1 * 11/2002 Kosley, Jr. et al.

FOREIGN PATENT DOCUMENTS

| EP | 533579 A1 | * | 3/1993 |
| EP | 617027 A1 | * | 9/1994 |
| EP | 847999 A1 | * | 6/1998 |

\* cited by examiner

*Primary Examiner*—Emily Bernhardt
(74) *Attorney, Agent, or Firm*—The Firm of Hueschen and Sage

(57) ABSTRACT

The present invention relates to a compound selected from those of formula (I):

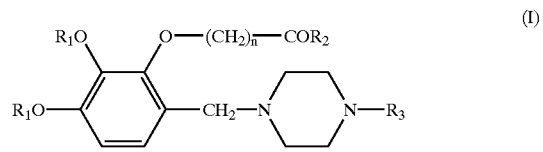

wherein:

$R_1$ represents alkyl,
$R_2$ represents hydroxy, alkoxy, or amino,
n represents an integer from 1 to 12 inclusive,
$R_3$ represents:
  hydrogen, optionally substituted alkyl, cycloalkyl, pyrimidinyl or optionally substituted phenyl, its isomers, and addition salts thereof with a pharmaceutically acceptable acid or base, medicinal products containing the same are useful in the prevention or treatment of acute and chronic cell ischaemia.

10 Claims, No Drawings

N-BENZYLPIPERAZINE COMPOUNDS

FIELD OF THE INVENTION

The present invention relates to new N-benzylpiperazine compounds and pharmaceutical compositions containing them.

DESCRIPTION OF THE PRIOR ART

The prior art is illustrated, for example, by:

French Patent Specifications 1 302 958 and 805 M which relate, respectively, to the preparation of N-trialkoxybenzylpiperazines and to the use of 2,3,4-trimethoxybenzylpiperazine as a medicament having vasodilatory activity, articles by Hiroshi Ohtaka et al., Chem. Pharm. Bull., 35, 2774–3275 (1987) and Chem. Pharm. Bull., 37, 11, 2124–3122 (1989) which mention trimetazidine compounds having a vasodilatory activity, and the synthesis of 1-[bis(4-fluorophenyl)methyl]-4-(2-hydroxy 3,4-dimethoxybenzyl)piperazine, an article by Tsuneo Kawashima et al., J. Pharmacobio-Dyn, 14, 449–459 (1991) relating to the isolation and identification of new metabolites of KB-2796, including 1-[bis(4-fluorophenyl)methyl]-4-(2-hydroxy 3,4-dimethoxybenzyl)piperazine, European Patent Specification EP 533 579 which describes N-benzylpiperazine compounds having an antihypoxic and antiischaemic activity, finally, European Patent Specification EP 617 027 which describes N-benzylpiperazine compounds for use in the treatment of neuronal diseases due to dysfunction of oxidative metabolism.

In addition to being new, the compounds of the present invention have especially innovative pharmacological activity and especially innovative therapeutic properties.

They enable, inter alia, the protection of mitochondria undergoing hypoxic stress, maintenance of the synthesis of ATP in organs starved of oxygen, such as protection of an isolated heart placed in an ischaemic situation. Finally, some are capable of crossing the blood-brain barrier. Those properties therefore make them useful in the prevention or treatment of acute and chronic cellular ischaemia, acute or chronic cerebral, cardiac or peripheral ischaemic accidents, whether followed by reperfusion or not, before any surgical intervention requiring a temporary interruption of blood circulation, locally or generally (tourniquet, clamp), in the treatment of chronic neurodegenerative diseases (such as senile dementia, latent or established Alzheimer's disease, cerebral ageing, amyotrophic lateral sclerosis, multiple sclerosis or Parkinson's disease) and in improving the storage of organs intended for transplantation and the resumption of functioning of transplants after reperfusion.

DETAILED DESCRIPTION OF THE INVENTION

The compounds of the invention also have markedly greater metabolic stability compared with all the compounds of similar structure already described, and thus provide better bioavailability.

More especially, the present invention relates to compounds of formula (I):

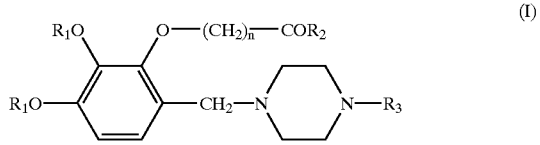

wherein:

$R_1$ represents a linear or branched $(C_1-C_6)$alkyl group, $R_2$ represents a hydroxy group, a linear or branched $(C_1-C_6)$alkoxy group, or an amino group (optionally substituted by one or two linear or branched $(C_1-C_6)$alkyl groups), n represents an integer from 1 to 12 inclusive.

$R_3$ represents:

a hydrogen atom, a linear or branched $(C_1-C_{12})$alkyl group optionally substituted by a phenyl group (itself optionally substituted by one or more identical or different substituents selected from halogen atoms and linear or branched $(C_1-C_6)$alkyl, linear or branched $(C_1-C_6)$alkoxy, hydroxy and trihalomethyl groups), a $(C_3-C_7)$cycloalkyl group, a carboxy group or a $(C_1-C_6)$alkoxycarbonyl group, a $(C_3-C_7)$cycloalkyl group, a pyrimidinyl group optionally substituted by one or two pyrrolidinyl groups, or a phenyl group optionally substituted by one or more identical or different substituents selected from halogen atoms and linear or branched $(C_1-C_6)$alkyl, linear or branched $(C_1-C_6)$alkoxy, hydroxy and trihalomethyl groups, their optical isomers and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The invention relates also to a process for the preparation of compounds of formula (I), characterised in that there is used as starting material a compound of formula (II):

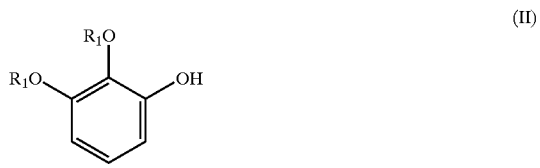

wherein $R_1$ is as defined for formula (I), which is reacted, in the presence of formaldehyde, with a substituted piperazine of formula (III):

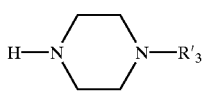 (III)

wherein R'₃ is as defined for R₃ with the exception of an alkyl group substituted by a carboxy group,
to yield a compound of formula (IV):

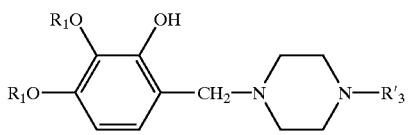 (IV)

wherein R₁ and R'₃ are as defined hereinbefore,
which is reacted with a compound of formula (V):

$$X-(CH_2)_n-COR'_2 \quad (V)$$

wherein X represents a halogen atom and R'₂ represents a linear or branched $(C_1-C_6)$alkoxy group, to yield a compound of formula (I/a), a particular case of the compounds of formula (I):

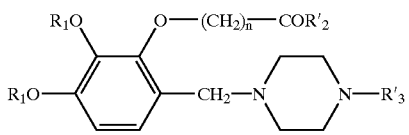 (I/a)

wherein R₁, R'₂, R'₃ and n are as defined hereinbefore, which compound of formula (I/a) is converted, if desired, to the corresponding mono- or di-acid of formula (I/b), a particular case of the compounds of formula (I):

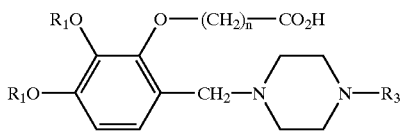 (I/b)

or to the corresponding amide of formula (I/c):

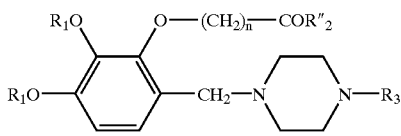 (I/c)

wherein R₁, R₃ and n are as defined for formula (I) and R''₂ represents an amino group optionally substituted by one or two linear or branched $(C_1-C_6)$alkyl groups,
which compounds of formulae (I/a), (I/b) and (I/c) are purified, if necessary, in accordance with a conventional purification technique, are separated, where appropriate, into their isomers, and are converted, if desired, into addition salts with a pharmaceutically acceptable acid or base.

The preferred compounds of the invention are those wherein R₁ represents a methyl group, R₂ represents a hydroxy group and R₃ represents a benzyl group, a pyrimidinyl group, a phenyl group preferably substituted by a methoxy group or a hydrogen atom.

The value n is preferably from 1 to 7. More especially, n is 6.

The preferred compounds of the invention are:

7-{6-[(4-benzyl-1-piperazinyl)methyl]-2,3-dimethoxyphenoxy}heptanoic acid and addition salts thereof, 7-{6-{[4-(pyrimidin-2-yl)-1-piperaziny])methyl}-2,3-dimethoxyphenoxy}heptanoic acid and addition salts thereof, 4-{6-[(piperazin-1-yl)methyl]-2,3-dimethoxyphenoxy}butyric acid and addition salts thereof, 7-{6-[(4-(2-methoxyphenyl)-1-piperazinyl)methyl]-2,3-dimethoxyphenoxy}heptanoic acid and addition salts thereof, 4-{6-[(4-(2-methoxyphenyl)-1-piperazinyl)methyl]-2,3-dimethoxyphenoxy}butyric acid and addition salts thereof.

The present invention relates also to pharmaceutical compositions comprising as active ingredient at least one compound of formula (I) alone or in combination with one or more inert, non-toxic excipients or carriers.

Among the pharmaceutical compositions according to the invention, there may be mentioned more especially those that are suitable for oral, parenteral, nasal, cutaneous administration, tablets or dragees, sublingual tablets, gelatin capsules, lozenges, suppositories, creams, ointments, dermal gels, etc.

The useful dosage varies according to the age and weight of the patient, the nature and severity of the disorder and the route of administration, and may be oral, nasal, rectal or parenteral. Generally, the unit dose ranges from 0.1 to 500 mg per 24 hours for treatment in from 1 to 3 administrations.

The following Examples illustrate the invention but do not limit it in any way.

The starting materials used are known products or are prepared according to known procedures.

The structures of the compounds described in the Examples were determined according to the usual spectrophotometric techniques (infrared, NMR, mass spectrometry, etc.).

EXAMPLE 1

Ethyl 7-{6-[(4-benzyl-1-piperazinyl)methyl]-2,3-dimethoxyphenoxy}-heptanoate dihydrochloride 2.2 g of 60% sodium hydride are suspended in a reactor containing 250 ml of anhydrous tetrahydrofuran cooled to 0° C. 17.1 g of 6-[(4-benzyl-1-piperazinyl)methyl]-2,3-dimethoxyphenol dissolved in 150 ml of anhydrous THF are added dropwise at room temperature to the preceding mixture, followed by 14.6 ml of ethyl 7-bromoheptanoate in 50 ml of anhydrous THF.

The reaction mixture is heated at reflux for 15 days and is then concentrated to dryness under a partial vacuum. The crude residue is taken up in diethyl ether and the precipitate obtained after cooling at 0° C. for 12 hours is filtered off and then washed with cold diethyl ether (4° C.).

The ethereal solutions are concentrated to dryness under a partial vacuum and yield a crude residue which is purified by chromatography over a silica column using a gradient of dichloromethane/methanol (98/2 to 90/10) to yield the expected product in the form of the base, which is converted to the corresponding dihydrochloride.

Melting point: 180° C.

Elemental Microanalysis:

|  | C % | H % | N % |
|---|---|---|---|
| Calculated | 60.94 | 7.76 | 4.90 |
| Found | 60.68 | 7.72 | 5.00 |

EXAMPLE 2

7-{6-[(4-Benzyl-1-piperazinyl)methyl]-2,3-dimethoxyphenoxy}-heptanoic acid dihydrochloride 10 g of the compound obtained in Example 1 are added to a solution containing 4 g of sodium hydroxide in 250 ml of ethanol. The whole is maintained for 6 hours without stirring. After removal of the solvent by evaporation, the residue is purified by chromatography over a silica column using a gradient of dichloromethane/methanol (95/5 to 0/100). The expected product is obtained in the form of the base and is converted to the corresponding dihydrochloride Melting point: 190° C.

Elemental Microanalysis:

|  | C % | H % | N % |
|---|---|---|---|
| Calculated | 59.66 | 7.42 | 5.15 |
| Found | 59.06 | 7.67 | 5.26 |

EXAMPLE 3

Ethyl {6-[(4-benzyl-1-piperazinyl)methyl]-2,3-dimethoxyphenoxy}-acetate dihydrochloride The expected product is obtained according to the process described in Example 1, replacing ethyl 7-bromoheptanoate by ethyl chloroacetate.

Melting point: 162° C.

Elemental Microanalysis:

|  | C % | H % | N % |
|---|---|---|---|
| Calculated | 57.49 | 6.83 | 5.59 |
| Found | 57.62 | 6.87 | 5.62 |

EXAMPLE 4

{6-[(4-Benzyl-1-piperazinyl)methyl]-2,3-dimethoxyphenoxy}acetic acid Dihydrochloride The expected product is obtained according to the process described in Example 2 starting from the compound described in Example 3.

Melting point: 175° C.

Elemental Microanalysis:

|  | C % | H % | N % |
|---|---|---|---|
| Calculated | 55.82 | 6.39 | 5.92 |
| Found | 55.31 | 6.37 | 5.86 |

EXAMPLE 5

Ethyl 4-{6-[(4-benzyl-1-piperazinyl)methyl]-2,3-dimethoxyphenoxy}-butyrate dihydrochloride The expected product is obtained according to the process described in Example 1, replacing ethyl 7-bromoheptanoate by ethyl 4-bromobutyrate.

Melting point: 164° C.

Elemental Microanalysis:

|  | C % | H % | N % |
|---|---|---|---|
| Calculated | 58.98 | 7.23 | 5.29 |
| Found | 59.32 | 7.18 | 5.06 |

EXAMPLE 6

4-{6-[(4-Benzyl-1-piperazinyl)methyl]-2,3-dimethoxyphenoxy}butyric acid dihydrochloride The expected product is obtained according to the process described in Example 2 starting from the compound described in Example 5.

Melting point: 200° C.

Elemental Microanalysis:

|  | C % | H % | N % |
|---|---|---|---|
| Calculated | 57.49 | 6.83 | 5.59 |
| Found | 57.48 | 7.00 | 5.61 |

EXAMPLE 7

Ethyl 8-{6-[(4-benzyl-1-piperazinyl)methyl]-2,3-dimethoxyphenoxy}-octanoate dihydrochloride The expected product is obtained according to the process described in Example 1, replacing ethyl 7-bromoheptanoate by ethyl 8-bromooctanoate.

Melting point: 177° C.

Elemental Microanalysis:

|  | C % | H % | N % |
|---|---|---|---|
| Calculated | 61.53 | 7.92 | 4.78 |
| Found | 61.40 | 7.92 | 4.79 |

EXAMPLE 8

8-{6-[(4-Benzyl-1-piperazinyl)methyl]-2,3-dimethoxyphenoxy}octanoic acid dihydrochloride The expected product is obtained according to the process described in Example 2 starting from the compound described in Example 7.

Melting point: 180° C.
Elemental Microanalysis:

|  | C % | H % | N % |
|---|---|---|---|
| Calculated | 60.32 | 7.59 | 5.02 |
| Found | 60.12 | 7.58 | 5.04 |

EXAMPLE 9

Methyl 10-{6-[(4-benzyl-1-piperazinyl)methyl]-2,3-dimethoxyphenoxy}-decanoate dihydrochloride The expected product is obtained according to the process described in Example 1, replacing ethyl 7-bromoheptanoate by methyl 10-bromodecanoate.
Melting point: 145° C.
Elemental Microanalysis:

|  | C % | H % | N % |
|---|---|---|---|
| Calculated | 62.09 | 8.07 | 4.67 |
| Found | 62.15 | 8.17 | 4.67 |

EXAMPLE 10

10-{6-[(4-Benzyl-1-piperazinyl)methyl]-2,3-dimethoxyphenoxy}-decanoic acid dihydrochloride The expected product is obtained according to the process described in Example 2 starting from the compound described in Example 9.
Melting point: 156° C.
Elemental Microanalysis:

|  | C % | H % | N % |
|---|---|---|---|
| Calculated | 61.53 | 7.92 | 4.78 |
| Found | 61.32 | 8.06 | 4.90 |

EXAMPLE 11

Methyl 11-{6-[(4-benzyl-1-piperazinyl)methyl]-2,3-dimethoxyphenoxy}-undecanoate dihydrochloride The expected product is obtained according to the process described in Example 1, replacing ethyl 7-bromoheptanoate by methyl 11-bromoundecanoate.
Melting point: 177° C.
Elemental Microanalysis:

|  | C % | H % | N % |
|---|---|---|---|
| Calculated | 62.63 | 8.21 | 4.57 |
| Found | 61.97 | 8.27 | 4.81 |

EXAMPLE 12

11-{6-[(4-Benzyl-1-piperazinyl)methyl]-2,3-dimethoxyphenoxy}-undecanoic acid dihydrochloride The expected product is obtained according to the process described in Example 2 starting from the compound obtained in Example 11.

Melting point: 185° C.
Elemental Microanalysis:

|  | C % | H % | N % |
|---|---|---|---|
| Calculated | 62.09 | 8.07 | 4.67 |
| Found | 61.97 | 8.06 | 4.71 |

EXAMPLE 13

Ethyl 7-{6-{[4-(pyrimidin-2-yl)-1-piperazinyl]methyl}-2,3-dimethoxyphenoxy}heptanoate dihydrochloride The expected product is obtained according to the process described in Example 1, replacing 6-[(4-benzyl-1-piperazinyl)methyl]-2,3-dimethoxyphenol by 6-{[4-(pyrimidin-2-yl)-1-piperazinyl]methyl}-2,3-dimethoxyphenol.
Melting point: 128° C.
Elemental Microanalysis:

|  | C % | H % | N % |
|---|---|---|---|
| Calculated | 55.81 | 7.21 | 10.01 |
| Found | 56.11 | 7.40 | 9.96 |

EXAMPLE 14

7-{6-{[4-(Pyrimidin-2-yl)-1-piperazinyl)methyl}-2,3-dimethoxyphenoxy}heptanoic acid dihydrochloride The expected product is obtained according to the process described in Example 2 starting from the compound described in Example 13.
Melting point: 115° C.
Elemental Microanalysis:

|  | C % | H % | N % |
|---|---|---|---|
| Calculated | 54.24 | 6.83 | 10.54 |
| Found | 54.33 | 6.90 | 10.63 |

EXAMPLE 15

Ethyl 7-{6-[(piperazin-1-yl)methyl]-2,3-dimethoxyphenoxy}heptanoate dihydrochloride The expected product is obtained according to the process described in Example 1, replacing 6-[(4-benzyl-1-piperazinyl)methyl]-2,3-dimethoxyphenol by 6-[(4-tert-butoxycarbonyl-1-piperazinyl)methyl]-2,3-dimethoxyphenol.

EXAMPLE 16

7-{6-[(Piperazin-1-yl)methyl]-2,3-dimethoxyphenoxy}heptanoic acid dihydrochloride The expected product is obtained according to the process described in Example 2 starting from the compound described in Example 15.

Melting point: 160° C.
Elemental Microanalysis:

|  | C % | H % | N % |
|---|---|---|---|
| Calculated | 52.98 | 7.56 | 6.18 |
| Found | 53.06 | 7.49 | 6.28 |

EXAMPLE 17

Ethyl 7-{6-[(4-phenyl-1-piperazinyl)methyl]-2,3-dimethoxyphenoxy}-heptanoate dihydrochloride The expected product is obtained according to the process described in Example 1, replacing 6-[(4-benzyl-1-piperazinyl)methyl]-2,3-dimethoxyphenol by 6-{[(4-phenyl)-1-piperazinyl]methyl}-2,3-dimethoxyphenol.

EXAMPLE 18

7-{6-[(4-Phenyl-1-piperazinyl)methyl]-2,3-dimethoxyphenoxy}-heptanoic acid dihydrochloride The expected product is obtained according to the process described in Example 2 starting from the compound described in Example 17.
Melting point: 132° C.
Elemental Microanalysis:

|  | C % | H % | N % |
|---|---|---|---|
| Calculated | 58.98 | 7.23 | 5.29 |
| Found | 58.96 | 7.32 | 5.25 |

EXAMPLE 19

Ethyl 7-{6-[4-cyclohexyl-1-piperazinyl)methyl]-2,3-dimethoxyphenoxy}-heptanoate dihydrochloride The expected product is obtained according to the process described in Example 1 replacing 6-[(4-benzyl-1-piperazinyl)methyl]-2,3-dimethoxyphenol by 6-[(4-cyclohexyl)-1-piperazinyl)methyl]-2,3-dimethoxyphenol.

EXAMPLE 20

7-{6-[4-Cyclohexyl-1-piperazinyl)methyl]-2,3-dimethoxyphenoxy}-heptanoic acid dihydrochloride The expected product is obtained according to the process described in Example 2 starting from the compound described in Example 19.
Melting point: 182° C.
Elemental Microanalysis:

|  | C % | H % | N % |
|---|---|---|---|
| Calculated | 58.31 | 8.28 | 5.23 |
| Found | 57.92 | 8.41 | 5.24 |

EXAMPLE 21

Ethyl 7-{6-[4-n-heptyl-1-piperazinyl)methyl]-2,3-dimethoxyphenoxy}-heptanoate dihydrochloride The expected product is obtained according to the process described in Example 1, replacing 6-[(4-benzyl-1-piperazinyl)methyl]-2,3-dimethoxyphenol by 6-[(4-n-heptyl)-1-piperazinyl)methyl]-2,3-dimethoxyphenol.

EXAMPLE 22

7-{6-[4-n-Heptyl-1-piperazinyl)methyl]-2,3-dimethoxyphenoxy}heptanoic acid dihydrochloride The expected product is obtained according to the process described in Example 2 starting from the compound described in Example 21.
Melting point: 152° C.
Elemental Microanalysis:

|  | C % | H % | N % |
|---|---|---|---|
| Calculated | 58.79 | 8.77 | 5.08 |
| Found | 58.84 | 8.80 | 4.87 |

EXAMPLE 23

Ethyl 7-{6-[4-cyclopropylmethyl-1-piperazinyl)methyl]-2,3-dimethoxyphenoxy}heptanoate dihydrochloride The expected product is obtained according to the process described in Example 1, replacing 6-[(4-benzyl-1-piperazinyl)methyl]-2,3-dimethoxyphenol by 6-[(4-cyclopropylmethyl)-1-piperazinyl)methyl]-2,3-dimethoxyphenol.

EXAMPLE 24

7-{6-[4-Cyclopropylmethyl-1-piperazinyl)methyl]-2,3-dimethoxyphenoxy}heptanoic acid dihydrochloride The expected product is obtained according to the process described in Example 2 starting from the compound described in Example 23.
Melting point: 170° C.
Elemental Microanalysis:

|  | C % | H % | N % |
|---|---|---|---|
| Calculated | 58.48 | 8.10 | 5.68 |
| Found | 58.20 | 8.11 | 5.53 |

EXAMPLE 25

Ethyl 5-{6-[(4-benzyl-1-piperazinyl)methyl]-2,3-dimethoxyphenoxy}pentanoate dihydrochloride The expected product is obtained according to the process described in Example 1, replacing ethyl 7-bromoheptanoate by ethyl 5-bromopentanoate.

EXAMPLE 26

5-{6-[(4-Benzyl-1-piperazinyl)methyl]-2,3-dimethoxyphenoxy}pentanoic acid dihydrochloride The expected product is obtained according to the process described in Example 2 starting from the compound described in Example 25.

Melting point: 181° C.

Elemental Microanalysis:

|  | C % | H % | N % |
|---|---|---|---|
| Calculated | 58.25 | 7.04 | 5.43 |
| Found | 58.28 | 7.07 | 5.47 |

EXAMPLE 27

Ethyl 6-{6-[(4-benzyl-1-piperazinyl)methyl]-2,3-dimethoxyphenoxy}hexanoate dihydrochloride The expected product is obtained according to the process described in Example 1, replacing ethyl 7-bromoheptanoate by ethyl 6-bromohexanoate.

EXAMPLE 28

6-{6-[(4-Benzyl-1-piperazinyl)methyl]-2,3-dimethoxyphenoxy}hexanoic acid dihydrochloride The expected product is obtained according to the process described in Example 2 starting from the compound described in Example 27.

Melting point: 173° C.

Elemental Microanalysis:

|  | C % | H % | N % |
|---|---|---|---|
| Calculated | 58.98 | 7.23 | 5.29 |
| Found | 59.05 | 7.33 | 5.36 |

EXAMPLE 29

Ethyl 4-{6-[(piperazin-1-yl)methyl]-2,3-dimethoxyphenoxy}-butyrate dihydrochloride The expected product is obtained according to the process described in Example 1, replacing 6-[(4-benzyl-1-piperazinyl)methyl]-2,3-dimethoxyphenol by 6-[4-tert-butoxycarbonyl-1-piperazinyl)methyl]-2,3-dimethoxyphenol and ethyl 7-bromoheptanoate by ethyl 4-bromobutyrate.

EXAMPLE 30

4-{6-[(Piperazin-1-yl)methyl]-2,3-dimethoxyphenoxy}butyric acid dihydrochloride

The expected product is obtained according to the process described in Example 2 starting from the compound described in Example 29.

Melting point: 141° C.

Elemental Microanalysis:

|  | C % | H % | N % |
|---|---|---|---|
| Calculated | 49.64 | 6.86 | 6.81 |
| Found | 49.24 | 6.91 | 5.81 |

EXAMPLE 31

Ethyl 4-{6-[(4-phenyl-1-piperazinyl)methyl]-2,3-dimethoxyphenoxy}butyrate dihydrochloride The expected product is obtained according to the process described in Example 1, replacing 6-[(4-benzyl-1-piperazinyl)methyl]-2,3-dimethoxyphenol by 6-[(4-phenyl-1-piperazinyl)methyl]-2,3-dimethoxyphenol and ethyl 7-bromoheptanoate by ethyl 4-bromobutyrate.

EXAMPLE 32

4-{6-[(4-Phenyl-1-piperazinyl)methyl]-2,3-dimethoxyphenoxy}-butyric acid dihydrochloride The expected product is obtained according to the process described in Example 2 starting from the compound described in Example 31.

Melting point: 129° C.

Elemental Microanalysis:

|  | C % | H % | N % |
|---|---|---|---|
| Calculated | 56.68 | 6.62 | 5.75 |
| Found | 56.68 | 6.75 | 5.81 |

EXAMPLE 33

Ethyl 7-{6-[(4-(2-methoxyphenyl)-1-piperazinyl)methyl]-2,3-dimethoxyphenoxy}heptanoate dihydrochloride The expected product is obtained according to the process described in Example 1, replacing 6-[(4-benzyl-1-piperazinyl)methyl]-2,3-dimethoxyphenol by 6-[4-(2-methoxyphenyl)-1-piperazinyl)methyl]-2,3-dimethoxyphenol.

EXAMPLE 34

7-{6-[(4-(2-Methoxyphenyl)-1-piperazinyl)methyl]-2,3-dimethoxyphenoxy}heptanoic acid dihydrochloride The expected product is obtained according to the process described in Example 2 starting from the compound described in Example 33.

Melting point: 141° C.

Elemental Microanalysis:

|  | C % | H % | N % |
|---|---|---|---|
| Calculated | 57.96 | 7.21 | 5.01 |
| Found | 57.70 | 7.22 | 5.02 |

EXAMPLE 35

Ethyl 4-{6-[(4-(2-methoxyphenyl)-1-piperazinyl)methyl]-2,3-dimethoxyphenoxy}butyrate dihydrochloride The expected product is obtained according to the process described in Example 1, replacing 6-[(4-benzyl-1- piperazinyl)methyl]-2,3-dimethoxyphenol by 6-[4-(2-methoxyphenyl)-1-piperazinyl)methyl]-2,3-dimethoxyphenol and ethyl 7-bromoheptanoate by ethyl 4-bromobutyrate.

EXAMPLE 36

4-{6-[(4-(2-Methoxyphenyl)-1-piperazinyl)methyl]-2,3-dimethoxyphenoxy}butyric acid dihydrochloride The expected product is obtained according to the process described in Example 2 starting from the compound described in Example 35.

Melting point: 153° C.
Elemental Microanalysis:

|  | C % | H % | N % |
|---|---|---|---|
| Calculated | 55.71 | 6.62 | 5.41 |
| Found | 55.83 | 6.62 | 5.37 |

EXAMPLE 37

Ethyl 4-{6-[(4-(pyrimidin-2-yl))-1-piperazinyl)methyl]-2,3-dimethoxyphenoxy}butyrate dihydrochloride The expected product is obtained according to the process described in Example 1, replacing 6-[(4-benzyl-1-piperazinyl)methyl]-2,3-dimethoxyphenol by 6-[4-(pyrimidin-2-yl)-1-piperazinyl)methyl]-2,3-dimethoxyphenol and ethyl 7-bromoheptanoate by ethyl 4-bromobutyrate.

EXAMPLE 38

4-{6-[(4-(2-Pyrimidin-2-yl)-1-piperazinyl)methyl]-2,3-dimethoxyphenoxy}butyric acid dihydrochloride The expected product is obtained according to the process described in Example 2 starting from the compound described in Example 37.

Melting point: 174° C.
Elemental Microanalysis:

|  | C % | H % | N % |
|---|---|---|---|
| Calculated | 51.54 | 6.18 | 11.45 |
| Found | 51.95 | 5.88 | 11.41 |

EXAMPLE 39

Ethyl 7-{6-[(4-(4-chlorobenzyl))-1-piperazinyl)methyl]-2,3-dimethoxyphenoxy}heptanoate dihydrochloride The expected product is obtained according to the process described in Example 1, replacing 6-[(4-benzyl-1-piperazinyl)methyl]-2,3-dimethoxyphenol by 6-[4-(4-chlorobenzyl)-1-piperazinyl)methyl]-2,3-dimethoxyphenol.

EXAMPLE 40

7-{6-[(4-(4-Chlorophenyl)-1-piperazinyl)methyl]-2,3-dimethoxyphenoxy}heptanoic acid dihydrochloride The expected product is obtained according to the process described in Example 2 starting from the compound described in Example 39.

Melting point: 187° C.
Elemental Microanalysis:

|  | C % | H % | N % |
|---|---|---|---|
| Calculated | 56.11 | 6.80 | 4.85 |
| Found | 55.98 | 6.86 | 5.03 |

EXAMPLE 41

Ethyl 4-{6-[(4-(4-chlorophenyl))-1-piperazinyl)methyl]-2,3-dimethoxyphenoxy}butyrate dihydrochloride The expected product is obtained according to the process described in Example 1, replacing 6-[(4-benzyl-1-piperazinyl)methyl]-2,3-dimethoxyphenol by 6-[4-(4-chlorobenzyl)-1-piperazinyl)methyl]-2,3-dimethoxyphenol and ethyl 7-bromoheptanoate by ethyl 4-bromobutyrate.

EXAMPLE 42

4-{6-[(4-(4-Chlorophenyl)-1-piperazinyl)methyl]-2,3-dimethoxyphenoxy}butyric acid dihydrochloride The expected product is obtained according to the process described in Example 2 starting from the compound described in Example 41.

EXAMPLE 43

Ethyl 4-{6-[(4-cyclohexyl-1-piperazinyl)methyl]-2,3-dimethoxyphenoxy}butyrate dihydrochloride The expected product is obtained according to the process described in Example 1, replacing 6-[(4-benzyl-1-piperazinyl)methyl]-2,3-dimethoxyphenol by 6-[(4-cyclohexyl)-1-piperazinyl)methyl]-2,3-dimethoxyphenol and ethyl 7-bromoheptanoate by ethyl 4-bromobutyrate.

EXAMPLE 44

4-{6-[(4-Cyclohexyl-1-piperazinyl)methyl]-2,3-dimethoxyphenoxy}butyric acid dihydrochloride The expected product is obtained according to the process described in Example 2 starting from the compound described in Example 43.

Melting point: 211° C.
Elemental Microanalysis:

|  | C % | H % | N % |
|---|---|---|---|
| Calculated | 55.98 | 7.76 | 5.68 |
| Found | 55.74 | 7.70 | 5.70 |

EXAMPLE 45

Ethyl 4-{6-[(4-n-heptyl-1-piperazinyl)methyl]-2,3-dimethoxyphenoxy}-butyrate dihydrochloride The expected product is obtained according to the process described in Example 1, replacing 6-[(4-benzyl-piperazinyl)methyl]-2,3-dimethoxyphenol by 6-[(4-n-heptyl-1-piperazinyl)methyl]-2,3-dimethoxyphenol and ethyl 7-bromoheptanoate by ethyl 4-bromobutyrate.

EXAMPLE 46

4-{6-[(4-n-Heptyl-1-piperazinyl)methyl]-2,3-dimethoxyphenoxy}butyric acid dihydrochloride The expected product is obtained according to the process described in Example 2 starting from the compound described in Example 45.

EXAMPLE 47

Ethyl 4-{6-[(4-cyclopropylmethyl-1-piperazinyl)methyl]-2,3-dimethoxyphenoxy}butyrate dihydrochloride The expected product is obtained according to the process described in Example 1, replacing 6-[(4-benzyl-piperazinyl)methyl]-2,3-dimethoxyphenol by 6-[(4-cyclopropylmethyl-1-piperazinyl)methyl]-2,3-dimethoxyphenol and ethyl 7-bromoheptanoate by ethyl 4-bromobutyrate.

EXAMPLE 48

4-{6-[(4-Cyclopropylmethyl-1-piperazinyl)methyl]-2,3-dimethoxyphenoxy}butyric acid dihydrochloride The expected product is obtained according to the process described in Example 2 starting from the compound described in Example 47.

EXAMPLE 49

Ethyl 3-{6-[(4-benzyl-1-piperazinyl)methyl]-2,3-dimethoxyphenoxy}-propionate dihydrochloride The expected product is obtained according to the process described in Example 1, replacing ethyl 7-bromoheptanoate by ethyl 3-bromopropionate.

EXAMPLE 50

3-{6-[(4-Benzyl-1-piperazinyl)methyl]-2,3-dimethoxyphenoxy}propionic acid dihydrochloride The expected product is obtained according to the process described in Example 2 starting from the compound described in Example 49.

EXAMPLE 51

Ethyl 7-{6-[(4-(2,6-dipyrrolidinyl-pyrimidin-4-yl)-1-piperazinyl)-methyl]-2,3-dimethoxyphenoxy}heptanoate tetrahydrochloride The expected product is obtained according to the process described in Example 1, replacing 6-[(4-benzyl-1-piperazinyl)methyl]-2,3-dimethoxyphenol by 6-[(4-2,6-dipyrrolidinyl-pyrimidin-4-yl)-1-piperazinyl)methyl]-2,3-dimethoxyphenol.

EXAMPLE 52

7-{6-[(4-(2,6-Dipyrrolidinyl-pyrimidin-4-yl)-1-piperazinyl)methyl]-2,3-dimethoxyphenoxy}heptanoic acid tetrahydrochloride The expected product is obtained according to the process described in Example 2 starting from the compound described in Example 51.

EXAMPLE 53

Ethyl 4-{6-[(4-(2,6-dipyrrolidinyl-pyrimidin-4-yl)-1-piperazinyl)-methyl]-2,3-dimethoxyphenoxy}butyrate tetrahydrochloride The expected product is obtained according to the process described in Example 1, replacing 6-[(4-benzyl-1-piperazinyl)methyl]-2,3-dimethoxyphenol by 6-[(4-(2,6-dipyrrolidinyl-pyrimidin-4-yl)-1-piperazinyl)methyl]-2,3-dimethoxyphenol and ethyl 7-bromoheptanoate by ethyl 4-bromobutyrate.

EXAMPLE 54

4-{6-[(4-(2,6-Dipyrrolidinyl-pyrimidin-4-yl)-1-piperazinyl)methyl]-2,3-dimethoxyphenoxy}butyric acid tetrahydrochloride The expected product is obtained according to the process described in Example 2 starting from the compound described in Example 53.

EXAMPLE 55

Ethyl 7-{6-[(4-n-(6-ethoxycarbonyl)hexyl-1-piperazinyl)methyl]-2,3-dimethoxyphenoxy}heptanoate dihydrochloride The expected product is obtained according to the process described in Example 1, replacing 6-[(4-benzyl-piperazinyl)methyl]-2,3-dimethoxyphenol by 6-[(4-n-(6-ethoxycarbonyl)hexyl-1-piperazinyl)methyl]-2,3-dimethoxyphenol.

EXAMPLE 56

7-{6-[(4-n-(6-Carboxy)hexyl-1-piperazinyl)methyl]-2,3-dimethoxyphenoxy}heptanoic acid dihydrochloride The expected product is obtained according to the process described in Example 2 starting from the compound described in Example 55.

EXAMPLE 57

Ethyl 4-{6-[(4-(3-ethoxycarbonyl)propyl-1-piperazinyl)methyl]-2,3-dimethoxyphenoxy}butyrate dihydrochloride The expected product is obtained according to the process described in Example 1, replacing 6-[(4-benzyl-piperazinyl)methyl]-2,3-dimethoxyphenol by 6-[(4-(3-ethoxycarbonyl)propyl-1-piperazinyl)methyl]-2,3-dimethoxyphenol and ethyl 7-bromoheptanoate by ethyl 4-bromobutyrate.

EXAMPLE 58

4-{6-[(4-(3-Carboxy)propyl-1-piperazinyl)methyl]-2,3-dimethoxyphenoxy}butyric acid dihydrochloride The expected product is obtained according to the process described in Example 2 starting from the compound described in Example 57.

EXAMPLE 59

Ethyl 7-{6-[(4-(3-ethoxycarbonyl)propyl-1-piperazinyl)methyl]-2,3-dimethoxyphenoxy}heptanoate dihydrochloride The expected product is obtained according to the process described in Example 1, replacing 6-[(4-benzyl-piperazinyl)methyl]-2,3-dimethoxyphenol by 6-[(4-(3-ethoxycarbonyl)propyl-1-piperazinyl)methyl]-2,3-dimethoxyphenol.

EXAMPLE 60

7-{6-[(4-(3-Carboxy)propyl-1-piperazinyl)methyl]-2,3-dimethoxyphenoxy}heptanoic acid dihydrochloride The expected product is obtained according to the process described in Example 2 starting from the compound described in Example 59.

EXAMPLE 61

Ethyl 4-{6-[(4-n-(6-ethoxycarbonyl)hexyl-1-piperazinyl)methyl]-2,3-dimethoxyphenoxy}butyrate dihydrochloride The expected product is obtained according to the process described in Example 1, replacing 6-[(4-benzyl-piperazinyl)methyl]-2,3-dimethoxyphenol by 6-[(4-n-(6-ethoxycarbonyl)hexyl-1-piperazinyl)methyl]-2,3-dimethoxyphenol and ethyl 7-bromoheptanoate by ethyl 4-bromobutyrate.

EXAMPLE 62

4-{6-[(4-n-(6-Carboxy)hexyl-1-piperazinyl)methyl]-2,3-dimethoxyphenoxy}butyric acid dihydrochloride The expected product is obtained according to the process described in Example 2 starting from the compound described in Example 61.

EXAMPLE 63

7-{6-[(4-Benzyl-1-piperazinyl)methyl]-2,3-dimethoxyphenoxy}-N,N-diethylheptanamide dihydrochloride 4.95 g of the compound described in Example 2 are dissolved in 100 ml of dichloromethane. 2.17 g of dicyclohexylcarbodiimide are added, followed by 2.1 ml of N,N-diethylamine and 1.28 g of N,N-dimethylaminopyridine. After stirring for 24 hours, the solution is filtered and then concentrated to dryness, and the resulting crude residue is purified by chromatography over a silica column using a gradient of ethyl acetate/methanol (100/0 to 80/20) to yield the expected product in the form of the base, which is converted to the corresponding dihydrochloride.

EXAMPLE 64

4-{6-[(4-Benzyl-1-piperazinyl)methyl]-2,3-dimethoxyphenoxy}-N,N-diethylbutanamide dihydrochloride The expected product is obtained according to the process described in Example 63 starting from the compound described in Example 6.

Melting point: 198° C.

Elemental Microanalysis:

|  | C % | H % | N % |
| --- | --- | --- | --- |
| Calculated | 60.41 | 7.79 | 7.55 |
| Found | 60.17 | 7.79 | 7.50 |

EXAMPLE 65

3-{6-[(4-Benzyl-1-piperazinyl)methyl]-2,3-dimethoxyphenoxy}-propionamide dihydrochloride The expected product is obtained from the compound described in Example 50, which is reacted in an ammoniacal medium.

Pharmacological Study of the Compounds of the Invention

A: Study of the Anti-Ischaemic Activity of the Compounds of the Invention

The model used is a model of transitory focal cerebral ischaemia produced by intraluminal occlusion which mimics an embolic cerebral vascular accident in humans. The location of the infarction is cortical and subcortical (R. Bordet et al., *J Cereb Blood Flow Metab.* 20, 2000, 1190–1196 and 1999, 19, 1309–1345).

The model consists of a unilateral occlusion of the middle carotid artery for 1 hour followed by reperfusion for 23 hours in an adult male Wistar rat. The aim of this experiment is to study the anti-ischaemic effect of the compounds of the invention.

The animals are anaesthetised for surgery with 300 mg/kg of chloral hydrate. For the duration of the surgery, their temperature is monitored and maintained at 37° C. using a temperature-controlled heating blanket.

The principal procedure is to stop the circulation of blood to the right middle cerebral artery (MCA) by intraluminal occlusion of the ostium. After 60 minutes, the occlusion is removed and the animals are replaced in their cage. After 24 hours the animals are sacrificed under anaesthetic. Their brains are removed rapidly and frozen, and 12 sections 50 $\mu$m thick and spaced 1 $\mu$m apart are obtained in a cryostat by stereotactic topography. The sections are stained with rapid cresyl violet. The unstained regions of the cerebral sections are defined as infarcted zones.

The uncorrected infarcted zones and the total hemispheric zones are calculated separately for each section using an image analysis program. The corrected total volume of infarction is calculated in order to compensate for the effect of cerebral cedema.

The product is administered in a dose of 1 mg/kg intravenously 3 minutes before occlusion.

In this model, the compounds of the invention and especially the compound of Example 2 reduced the size of the infarction of the cortex and striatum significantly, indicating a neuroprotective effect.

B: Hypoxia of Astrocytes in Culture

Experimental Protocol:

The astrocyte cultures are obtained from newborn rats in accordance with the technique described by Booher and Sensenbrenner (Neurobiology, 1972, 2, 97–105).

They are used three to six weeks after being placed in culture in accordance with a hypoxia model described by Plateel et al. (J. Neurochem. 1995, 65, 2138–2145). The medium is changed 24 hours before the start of hypoxia in order to reconstitute the ATP reserves. After the addition of culture medium that has been degassed of $O_2$ and that contains a given concentration of test molecules, hypoxia is produced in an anaerobic chamber for a duration of 24 hours. The concentration of ATP is determined using luminescence and is expressed in picomoles of ATP/milligram of protein.

In this model, for degrees of hypoxia ranging from 27% to 79%, the compound of Example 2 enables recovery of ATP ranging from 35 to 87%, whereas trimetazidine has no effect on this parameter. The maximum effect is observed at 1 $\mu$M.

C: Neuroprotection in the Cortex and White Matter by the Compounds of the Invention The model used is a mouse model of neurodegeneration affecting both the cortical neurones and the subjacent white matter (S. L. Tahraoui et al., Brain Pathol., 2001, 11, 56–71). This model is based on an intracerebral injection of S-bromo-willardiine, a glutamatergic agonist that acts on AMPA-kainate receptors, or of ibotenate, an agonist of NMDA-type receptors, in the newborn mouse.

All the injections are carried out in the morning between 10.00 and 13.00 hours. The animals are anaesthetised in advance and kept under a heating lamp during the handling period. Each experimental group comprises from 5 to 12 Swiss mice of both sexes, from at least 2 different litters. On the 5th day of life (P5), 10 µg of ibotenate or 15 µg of S-bromo-willardiine are injected intracerebrally using a 25G gauge needle mounted on a 50 µl syringe, fixed to a calibrated device that delivers a bolus of 1 µl at each depression. The needle is inserted 2 mm below the cutaneous level, in the fronto-parietal region of the right hemisphere (2 mm in front of the lambdoid suture and 2 mm outside the median line). Two boluses of 1 µl (1 µl into the periventricular white matter and 1 µl into the cortex) are administered. An interval of 30 seconds, during which the needle remains in position, separates each bolus in order to allow diffusion of the product. Immediately after this excitotoxic assault, the test compound (3, 10 or 30 mg/kg) or the carrier is administered intraperitoneally (injected volume=5 µl). The animals are sacrificed by decapitation 5 days later (P10) and their brains are immediately removed and fixed in formol before being enclosed in paraffin. Series of 15 µm coronal sections are prepared for all the brains and stained with cresyl violet, which makes it possible to determine in a precise and reproducible manner the anterio-posterior axis of the histological lesions in both the cortex and the white matter. The sizes of the histological lesions are determined by two independent observers having no knowledge of the experimental groups. The results are expressed in the form of averages.

In this model, the compound of Example 2 especially reduced the size of the lesions in the white matter and in the cortex, which indicates an important neuroprotective effect. Trimetazidine (TMZ), which is tested by way of comparison, has a very low neuroprotective effect.

|  | Cortical lesions | | | White matter lesions | | |
|---|---|---|---|---|---|---|
| Product 10 mg/kg i.p. | control | TMZ | compound of Example 2 | Control | TMZ | compound of Example 2 |
| Number of animals | 19 | 7 | 6 | 18 | 7 | 6 |
| lesion, µm | 850.5 | 800 | 200 | 480 | 320 | 146.7 |

D: Metabolic Stability

The model used to estimate metabolic stability was developed and validated in isolated rat and human microsomes (M. Bertrand et al., European Journal of Pharmaceutical Sciences, 2000, Vol 11, Suppl. 2, S61–S72).

The prediction of metabolic bioavailability (MF %) is based on the in vitro measurement of the metabolic stability using hepatic microsomes and assuming total absorption. Briefly, the product is incubated at $10^{-7}$M in the presence of rat and human hepatic microsomes (0.33 mg of protein/ml) for 0, 5, 15, 30 and 60 minutes. At each point in time, the amount of unchanged product is measured by LC-MS-MS. The in vitro intrinsic clearance (Clint) corresponds to the curve (after LN linearisation) of the residual concentration of unchanged product over the incubation time. That in vitro intrinsic clearance is then scaled up to the entire organism in in vivo intrinsic clearance (vivoClint) using factors of 0.045 mg of prot/kg of liver and a liver weight of 11 g for the rat and of 1.2 kg for humans. The conversion of in vivo intrinsic clearance to hepatic clearance (HepCl) is achieved using a model of venous equilibrium (HepCl=vivoClint*HBF/(vivoClint+HBF) wherein HBF (hepatic blood flow) corresponds to 22 ml/min for the rat and 1500 ml/min for humans. The MF % is then derived from the coefficient of hepatic extraction using the following formula:

MF %=1−HepCl/HBF.

That method gives a good correlation between the in vitro and in vivo data. In this model, the compounds of the invention demonstrated very good metabolic stability.

E—Anti-Apoptotic Effect

An in vitro study into an anti-apoptotic effect in primary cultures of cardiomyocytes was carried out by inducing apoptosis by adding hydrogen peroxide ($H_2O_2$). The free radicals produced induce apoptosis. This is similar to what is observed in ischaemia-reperfusion (R. Von Harsdorf, Circulation 99, 2934–2941).

The cardiomyocytes are isolated from newborn rat hearts and are spread out at a density of 35 000 cells/cm². The process of apoptosis is induced by the addition of $H_2O_2$ (0.075 mmol/liter) for 30 minutes. The cardiomyocytes are then replaced in the culture medium for 24 hours. The apoptotic cells are visualised by various techniques, for example by the fragmentation of the genomic DNA that occurs in the process of apoptosis. It is shown by the following two techniques (see above for reference):

1. The TUNEL test enables labelling of the cell nuclei exhibiting fragmentation of their DNA.
2. The fragmentation of the DNA is demonstrated by the "DNA laddering" technique. The characteristic fragments of 180 bp of genomic DNA are detected by electrophoresis on agarose gel.

The migration of phosphatidylserine (PS) from the inside of the membrane of the cell nucleus to the outside (externalisation) is an early indicator of apoptosis. This can be visualised by fluorescent labelling using annexin-V-FITC (fluorescein isothiocyanate) and quantified by comparison with the total number of cells.

In this in vitro model, the compound of Example 2 protects the cardiomyocytes against apoptosis. The effect manifests itself in a decrease in the percentage of cells undergoing apoptosis and in an increase in cell survival. As a consequence, the product is a cardioprotective product.

F—Neuroprotection in the CA1 and CA3 Regions of the Hippocampus

Kainic acid is one of the most potent exogenous excitotoxins in existence, which is demonstrated by its ability to induce acute or sub-acute epileptiform disorders. The histopathological changes observed which are associated with administration of kainic acid differ from cerebral ischaemia caused by lesions that develop first in the CA1 to CA3 regions of the hippocampus (C. Montecot et al., Neuroscience 84, 791–800). The aim is to study the protective effect against lesions induced essentially in the CA3 region of the hippocampus while there is no reduction in the circulation of blood.

Kainic acid is administered intraperitoneally to a conscious rat in a dose of 12 mg/kg. The animal is then observed for a period of about 2 hours during which, after a latent period, epileptiform convulsions occur. At the end of 2 hours, the convulsions are stopped by administration of 10 mg/kg of diazepam. The animals are sacrificed 7 days later, their brains are isolated and 8 transverse sections 15 µm thick, spaced 150 µm apart, are prepared. These are analysed by contrast microscopy by two independent observers having no knowledge of the experimental groups. A rating of 0 to 3 is given according to the severity of the neuronal lesions. The ratings for each hemisphere are added together to obtain a lesion rating.

The product is administered in a dose of 20 mg/kg by the intraperitoneal route 3 minutes before administration of the kainic acid.

In this model, a single injection of the compound of Example 2 protects the neurones of the CA1 and CA3 regions of the hippocampus against lesions induced by kainic acid and thus demonstrates a strong neuroprotective effect.

Pharmaceutical Composition:

Formulation for the preparation of 1000 tablets each containing a dose of 10 mg

| | |
|---|---|
| Compound of Example 2 | 10 g |
| Hydroxypropylcellulose | 2 g |
| Wheat starch | 10 g |
| Lactose | 100 g |
| Magnesium stearate | 3 g |
| Talc | 3 g |

What is claimed is:

1. A compound selected from those of formula (I):

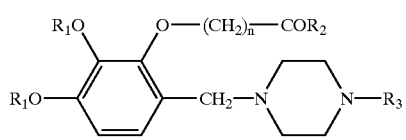

wherein:
  $R_1$ represents linear or branched $(C_1-C_6)$alkyl,
  $R_2$ represents hydroxy, linear or branched $(C_1-C_6)$alkoxy, or amino, optionally substituted by one or two linear or branched $(C_1-C_6)$alkyl groups,
  n represents an integer from 1 to 12 inclusive,
  $R_3$ represents:
    hydrogen,
    linear or branched $(C_1-C_{12})$alkyl optionally substituted by phenyl, which may be optionally substituted by one or more identical or different substituents selected from halogen and linear or branched $(C_1-C_6)$alkyl, linear or branched $(C_1-C_6)$alkoxy, hydroxy and trihalomethyl, or said alkyl is optionally substituted by $(C_3-C_7)$cycloalkyl, carboxy or $(C_1-C_6)$alkoxy-carbonyl,
    $(C_3-C_7)$cycloalkyl,
    pyrimidine optionally substituted by one or two pyrrolidinyl groups, or
    phenyl optionally substituted by one or more identical or different substituents selected from halogen and linear or branched $(C_1-C_6)$alkyl, linear or branched $(C_1-C_6)$alkoxy, hydroxy and trihalomethyl,
  its optical isomers, or an addition salt thereof with a pharmaceutically acceptable acid or base.

2. A compound of claim 1 wherein $R_1$ represents methyl.

3. A compound of claim 1 wherein $R_3$ is alkyl substituted by phenyl, pyrimidinyl, phenyl or hydrogen.

4. A compound of claim 1 wherein n is an integer from 1 to 7.

5. A compound of claim 4 wherein n is 6.

6. A compound of claim 1 wherein $R_2$ represents hydroxy.

7. A compound of claim 1 which is 7-{6-[(4-benzyl-1-piperazinyl)methyl]-2,3-dimethoxyphenoxy}heptanoic acid, or an addition salt thereof.

8. A compound of claim 1 selected from 7-{6-{[4-(pyrimidin-2-yl)-1-piperaziny])methyl}-2,3-dimethoxyphenoxy}heptanoic acid, 4-{6-[(piperazin-1-yl)methyl]-2,3-dimethoxy-phenoxy}butyric acid, 7-{6-[(4-(2-methoxyphenyl)-1-pipera-zinyl)methyl]-2,3-amethoxy}heptanoic acid, 4-{6-[(4-(2-methoxyphenyly)-1-Piperazinyl)methyl]-2,3-dimethoxyphenoxy}butyric acid, or an addition salt thereof.

9. A method for treating an animal or human living body, tissue, or organ afflicted with or vulnerable to an ischemic condition resulting from acute and chronic cell ischaemia, acute or chronic cerebral, cardiac or peripheral ischaemic accidents, whether followed by reperfusion or not, the ischemia incident to any surgical intervention requiring a temporary interruption of blood circulation, the ischemia associated with or resulting in chronic neurodegenerative diseases, the ischemia incident to the storage of organs intended for transplantation, or the ischemia incident to the resumption of functioning of transplant organs after reperfusion, comprising the step of administering to the animal, human living body, tissue or organ and amount of a compond of claim 1 which is effective for alleviation of the condition.

10. A pharmaceutical composition comprising as active principle an effective amount of a compound of claim 1 together with one or more pharmaceutically acceptable excipients or vehicles.

* * * * *